United States Patent [19]

Gibson et al.

[11] 4,386,095

[45] May 31, 1983

[54] DIAMINOPYRIDINES TO IMPROVE COGNITION

[75] Inventors: Gary E. Gibson, Larchmont; Christine J. Peterson, Yonkers, both of N.Y.

[73] Assignee: Cornell Research Foundation, Inc., Ithaca, N.Y.

[21] Appl. No.: 351,087

[22] Filed: Feb. 22, 1982

[51] Int. Cl.³ ............................................. A61K 31/44
[52] U.S. Cl. ................................................... 424/263
[58] Field of Search ......................................... 424/263

[56] References Cited

PUBLICATIONS

Gibson et al., Neuroscience Abstr., 7:187 (1981).
Gibson et al., Fed. Proc., 65 200 (1981).
Drachman et al., Neurobiology of Aging, 1:39 (1981).
Drachman, Neurology, 27-783 (1977).
Lundh et al., Neurol. Neurosurg., Psychiat. 40 1109 (1977).
Agoston et al., Anaesth. 50:383 (1978).
Lundh et al., Neurol. Neurosurg., Psychiat. 42:171 (1979).
Davies et al., Brain Res. 138:385 (1978).
Gibson et al., International Soc. Neurochem. 8-386 (1981).
Arehart-Treichel, Science News, 120:378 (1981).
Gibson et al., Biochem. Pharm. 31:111 (1982).

Primary Examiner—Stanley J. Friedman
Attorney, Agent, or Firm—Sughrue, Mion, Zinn, Macpeak & Seas

[57] ABSTRACT

Diaminopyridines improve cognition in aged animals. 3,4-Diaminopyridine is disclosed as a preferred compound to improve the decreased cognitive function which accompanies aging. It is believed that the diaminopyridines improve cognition by affecting nervous system acetylcholine metabolism.

10 Claims, 1 Drawing Figure

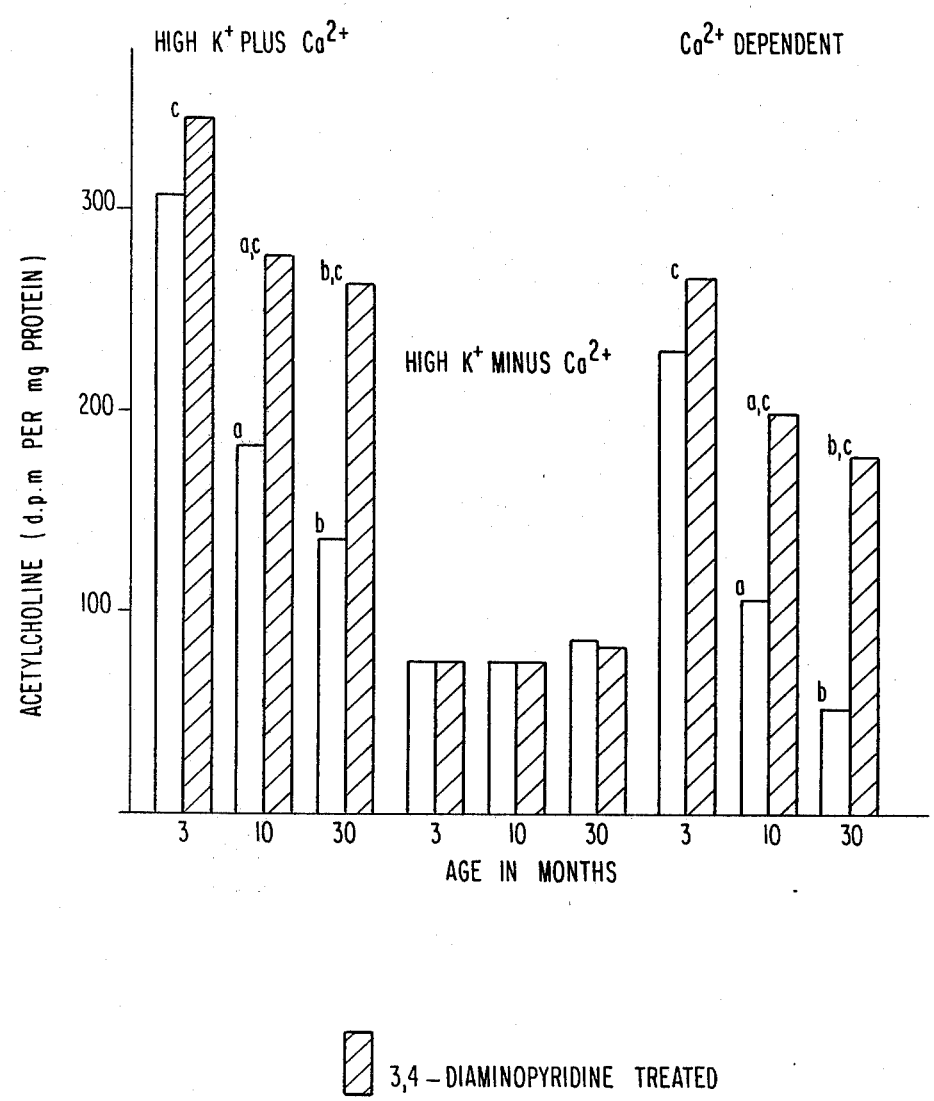

DIAMINOPYRIDINES TO IMPROVE COGNITION

The invention described herein was made in the course of work under grants NS03346-20 and NS16997-02 from the United States Department of Health and Human Services.

BACKGROUND OF THE INVENTION

The generality of a decreased cognitive function in man with senescence is well accepted. The same phenomenon has been observed and documented in many lower mammals, including those routinely employed in pharmacological testing programs for screening and predicting usefulness in higher mammals, including humans.

Factors such as decreased acetylcholine synthesis and impairment of cholinoreceptive neurons in aged animals have been related to decreased cognitive function. Similarly, choline supplementation of 10 month old mice improves performance on passive avoidance tasks. Even so, the molecular basis of the decreased cognitive function is higher animals is unknown. P. Davies, and A. Verth, *Brain Res.* 138: 395 (1978); T. D. Reisine, H. I. Yamamura, E. D. Bird, E. Spokes and S. J. Enna, *Brain Res.* 159: 447 (1978); P. I. White, M. J. Goodhardt, J. P. Kent, C. R. Hiley, L. H. Carrasco, I. E. Williams, and D. M. Bowen, *Lancet i:* 668 (1977); E. McGeer and P. L. McGeer, IN: Aging Vol. 3; *Neurobiology of Aging* (R. D. Terry and S. Gershon, Eds. p. 384 (1977); E. K. Perry, R. H. Perry, P. Gibson, G. Blessed and B. E. Tomlinson, *Neurosci. Lett.* 6: 85 (1977); N. Sims, D. M. Bowen and A. N. Davison, *Biochem. J.*, 196: 867 (1981); A. S. Lippa, R. W. Pelham, B. Beer, D. J. Critchett, R. L. Dean, and R. T. Bartus, *Neurobiology of Aging* 1: 13 (1980); R. T. Bartus, R. L. Dean, J. A. Goas and A. S. Lippa, *Science* 209: 301 (1981).

Related work by the present inventors has shown that during hypoxia, pharmacological agents that enhance calcium influx into nerve terminals (e.g., 4-aminopyridine and 3,4-diaminopyridine) partially restore cholinergic activity and behavior by stimulation of the calcium dependent release of acetylcholine. G. E. Gibson and C. Peterson, *Fed. Proc.* 65: 200 (1981); G. E. Gibson and C. Peterson, *Biochem. Pharm.* 32: 111 (1982); C. Peterson, C. J. Pelmas and G. E. Gibson, *Neurosci. Abstr.* 7, 494 (1981). Cholinergic deficits occur during mild acute hypoxia. Low oxygen tensions impair memory in man, produce behavioral deficits in animals and reduce the synthesis and the calcium dependent release of acetylcholine in animals.

Further, pharmacological interruption of the cholinergic system produces decreases in cognition similar to those during senescence and mild acute hypoxia. D. A. Drachman, *Neurology* 27: 783 (1977); D. A. Drachman, D. Noffsinger, B. J. Sahakian, S. Krudziel and P. Fleming, *Neurobiology of Aging* 1: 39 (1981).

Prior to this invention and their related work on hypoxia, the present inventors were not aware of the use of any diaminopyridines in the treatment of any disease or condition in man or lower animals. 4-aminopyridine has been used to treat disorders of neuromuscular transmission, e.g., botulinum toxin poisoning and myasthenia gravis. H. Lundh, O. Nilsson and I. J. Rosen, *Neurol. Neurosurg. Psychiat.* 40: 1109 (1977); S. Agoston, P. Van Weerden and A. Broekert, *Anaesth.* 50: 383 (1978); H. Lundh, O. Nilsson and I. J. Rosen, *Neurol. Neurosurg. Psychiat.* 42: 171.

BRIEF DESCRIPTION OF THE DRAWING

The FIGURE of the Drawing is a graph of the results obtained in Example 2.

SUMMARY OF THE INVENTION

It is an object of the present invention to provide a class of chemical compounds that ameliorate the decreased cognitive function associated with aging.

A further object of this invention is to provide a process for treating age-related neurochemical and behavioral deficits in mammals.

Still another object of this invention is to provide a class of chemical compounds which stimulate the calcium-dependent, potassium-stimulated release of acetylcholine by neurons.

In accordance with the present invention, it has now been found that diaminopyridines reverse the decreased cognitive function associated with aging.

In one embodiment of the present invention at least one diaminopyridine is administered to a subject in an amount effective to ameliorate or temporarily reverse age-related behavioral deficits, particularly cognition and awareness.

In another embodiment of this invention, at least one diaminopyridine is administered to a subject in an amount sufficient to increase the calcium-dependent, potassium-stimulated release of acetylcholine in the area of nerve tissue. Thus, in this embodiment of the invention, the use of the diaminopyridines is not limited to geriatric use but the compounds can be administered wherever decreased acetylcholine metabolism is associated with a cognitive deficiency, such as Alzheimer's disease, although unrelated to advanced age.

In a preferred embodiment of the present invention, 3,4-diaminopyridine is administered to a subject in an amount effective to increase acetylcholine metabolism.

DETAILED DESCRIPTION OF THE INVENTION

The present invention relates to the use of a class of chemical compounds to increase the availability of acetylcholine in the vicinity of nerve tissue. Decreased acetylcholine metabolism has now been associated with the decreased cognition which occurs with aging and in some disease states. A similar relationship has been found in hypoxic animals, that is mild acute hypoxia also reduces cognition, with reduced acetylcholine metabolism being observed.

The administration of the compounds of this invention ameliorates and/or at least temporarily reverses cognitive deficits observed in aged animals. Although the present inventors do not wish to be bound by any particular theory, their in vitro work supports a theory that the compounds used in this invention exhibit their beneficial properties through increasing calcium dependent acetylcholine release at the neuron level.

The compounds used in the present invention are the diaminopyridines, which can be represented by formula (I):

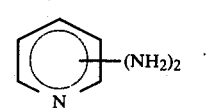

(I)

The two NH₂ moieties can be positioned at any two ring positions other than the nitrogen position. From a subgeneric standpoint, the preferred sub-group of compounds is that wherein the amino groups are at adjacent ring positions. A preferred compound is 3,4-diaminopyridine.

Compounds of the present invention are known in the art. Any particular isomer which is not disclosed in the art would be synthesized using procedures known in the art.

As representative compounds, there may be mentioned 2,3-diaminopyridine; 2,5-diaminopyridine; 2,6-diaminopyridine; 3,4-diaminopyridine; 4,5-diaminopyridine, and 4,6-diaminopyridine.

Although compounds of the formula (I) do not contain any substituents on the amino nitrogen atoms other than hydrogen and do not carry any substituents on the aromatic ring other than the two primary amino groups, it is contemplated that substitutents could be present which would affect the desired activity of the compounds in a positive manner.

The compounds of the present invention can be formulated into various types of pharmaceutical preparations for administration. As far as is known, the compounds of the present invention are solids which are highly water soluble when pH adjusted. Thus, aqueous-based liquid formulations can be prepared for oral and injection use. Also, tablet and capsule preparations can be prepared by admixing the active ingredient with conventional fillers and excipients such as starch, lactose, and the like, and then using the powder in conventional tabletting and capsule-making processes.

The diaminopyridine would be administered in a dosage sufficient to increase the calcium-dependent, potassium-stimulated acetylcholine release in the vicinity of nerve tissue. An optimum dosage as well as dosage range for a particular compound can be determined using the lower animal testing procedures in the examples, herebelow. Even so, a suggested dosage range is about 1 to 10,000 picomoles (molecular weight is 114) per Kg body weight, preferably about 1 to 10 picomoles per Kg body weight. This dosage could be administered up to 12 times a day to maintain a continuum of activity. Indeed, the present invention, particularly where used for long term therapy lends itself to sustained release modes. In addition to the usual types of oral sustained release preparations, solid injectables such as the subcutaneous pellet type may be desirable.

EXAMPLE 1

The usefulness of the compounds of this invention is illustrated by the mouse tight rope test. In this test, aged BALB/cNNia mice (obtained from the National Institute on Aging Colony) 3, 10 and 30 months old, were evaluated on their ability to traverse an elevated taut string. Each animal was evaluated prior to the test and received points for use of paws and tail, for changing position, traveling along the string or reaching one of two vertical poles in less than one minute but lost points for freezing or for falling before one minute. See further description in L. L. Barclay, G. E. Gibson and J. P. Blass, Pharm. Biochem. Behav. 14: 153 (1981). The scores in this instance ranged from −5 to +12 points. Multiple testing of the animals did not alter their performance. The skilled artisan can vary the test protocol but should obtain analogous results. In order to minimize bias due to the order of drug dosage and time of testing, the mice were rotated on the treatments.

The animals from each age group, 3, 10 and 30 months of age were subdivided into groups of three mice each. All of the mice were pretested and those with scores of less than 10 were used in the drug trial about one hour later. Over a period of 12 days, each group was rotated and did not receive the same treatment more than once. Testing commenced on day 1 and there was a minimum of three non-test days between sessions.

Initially, the tight rope test was given at different times (5, 10 or 15 minutes) after intraperitoneal injection of 3,4-diaminopyridine at the dosage that was optimal for improvement of behavior in hypoxic mice (10 picomole/kg, herein abbreviated as "pmole/kg"). Table 1 sets forth the results of this initial test. The "time of tight rope test" represents the interval between the injection of the test drug and the time of the test. "Initial" value is the mean±S.E.M. of 18 observations (about six observations for each of the three mice of the group) taken about one hour prior to drug administration. "Final" value was determined in the same manner. "Change" is the numerical difference between "Initial" and "Final" values. Significance was determined by analysis of variance with the least significant difference test ($p<0.05$).

TABLE 1

| Time of | Tight Rope Test Score | | |
|---|---|---|---|
| Tight Rope Test | Initial | Final | Change |
| | 3 Months | | |
| 5 min | 11.2 ± 0.3 | | |
| 10 min | 11.2 ± 0.2 | | |
| 15 min | 10.9 ± 0.3 | 11.3 ± 0.1 | 0.4 ± 0.3 |
| | | 10 Months | |
| 5 min | 4.3 ± 0.2[a] | 9.5 ± 0.5[c] | 5.1 ± 0.5[a] |
| 10 min | 3.2 ± 0.6[a] | 6.8 ± 1.0[c] | 3.5 ± 1.0[a] |
| 15 min | 4.0 ± 0.8[a] | 5.7 ± 0.8[c] | 1.6 ± 1.2 |
| | | 30 Months | |
| 5 min | −0.3 ± 0.9[b] | 9.0 ± 0.7 | 9.3 ± 1.0[b] |
| 10 min | −0.9 ± 0.4[b] | 6.3 ± 0.8[c] | 7.2 ± 0.8[b] |
| 15 min | −1.3 ± 0.3[b] | 5.9 ± 0.7[c] | 7.2 ± 0.7[b] |

From the above test results, five minutes after drug injection appears to be the optimal time for testing. Further tests were carried out in the same manner using the same (10 pmole/kg) and other dosages of 3,4-diaminopyridine, but with the "Final" test score always determined five minutes after drug administration. This time, nine observations (three for each mouse) were taken with test scores determined as above. The results are set forth in Table 2.

TABLE 2

| Drug Dosage (pmol/kg) | Tight Rope Test Score | | |
|---|---|---|---|
| | 3 Months | | |
| 10000 | 11.7 ± 1.7 | | |
| 100 | 10.6 ± 0.5 | 11.6 ± 0.2 | 1.0 ± 0.6 |
| 10 | 10.2 ± 0.3 | 11.0 ± 0.8 | 1.0 ± 0.5 |
| 1 | 10.4 ± 0.2 | 11.7 ± 0.3 | 1.3 ± 0.5 |
| 0.01 | 11.4 ± 0.2 | | |
| | | 10 Months | |
| 10000 | 3.7 ± 0.5[a] | 5.8 ± 0.3 | 1.7 ± 0.3 |
| 100 | 3.8 ± 0.6[a] | 8.3 ± 0.7[c] | 4.5 ± 0.5[a] |
| 10 | 4.3 ± 0.3[a] | 8.9 ± 0.5[c] | 4.8 ± 0.5[a] |
| 1 | 4.0 ± 0.7[a] | 8.9 ± 1.1[c] | 4.9 ± 1.4[a] |
| 0.01 | 4.0 ± 0.6[a] | 5.9 ± 0.9 | 1.9 ± 1.1 |
| | | 30 Months | |
| 10000 | −0.2 ± 0.4[b] | 1.4 ± 0.5 | 1.9 ± 0.6 |
| 100 | −2.2 ± 0.2[b] | 7.6 ± 0.8[c] | 9.8 ± 0.9[b] |
| 10 | −0.1 ± 0.4[b] | 8.9 ± 1.7[c] | 9.4 ± 0.8[b] |
| 1 | −0.8 ± 1.2[b] | 7.8 ± 1.0[c] | 8.8 ± 1.1[b] |

TABLE 2-continued

| Drug Dosage (pmol/kg) | Tight Rope Test Score | | |
|---|---|---|---|
| 0.01 | −1.2 ± 0.3[b] | 0.8 ± 0.2 | 2.0 ± 0.3 |

[a]Denotes value differs from 3 month old mice.
[b]Denotes value differs from 3 and 10 month old mice.
[c]Denotes value differs from non-drug treated aged matched mice.

EXAMPLE 2

This experiment was carried out in triplicate using the reagents and release techniques described by the inventors in J. Neurochem. 37: 978 (1981). Aged BALB/c NNia mice (3, 10 and 30 months) obtained from the National Institute on Aging Colony were used. The mice were decapitated and the forebrain rostral to the cerebellum and pons without the olfactory bulbs were removed, sliced in two dimensions with a McIlwain Chopper and the brain slices were preincubated in tubes for one hour at 37° C. with constant shaking in low potassium (5 mM) buffer containing 5 mM-[U-$^{14}$C]-glucose (1 Ci/mole), 40 μM-paraoxon (diethyl 4-nitrophenyl phosphate) and 50 μM-choline chloride. Preincubations were terminated by cooling; the supernatant and subsequent rinses with nonradioactive ice cold buffer were removed after centrifugation. Twelve tubes are run simultaneously for each mouse for each single test.

The prelabeled acetylcholine was released using incubation medium A in one-half of the tubes and incubation medium B in the other half. Incubation medium A (1 ml) contained 2.3 mM calcium. Incubation medium B (1 ml) contained 1 mM EGTA (ethyleneglycol bis(β-aminoethylether)N,N' tetraacetic acid). All tubes were then flushed for ten minutes with 100% oxygen and thereafter a depolarizing solution of potassium (31 mM) was added to each tube. Finally, 10 nM 3,4-diaminopyridine was added to each set of tubes. All tubes were incubated at 37° C. for 10 minutes to release acetylcholine. The incubation was terminated by cooling and the supernatant removed after centrifugation. Radioactive acetylcholine was extracted from the supernatant and expressed as disintegrations per mg protein. Only release under high potassium (31 mM) was evaluated since resting release did not change with aging.

The results of this experiment are illustrated graphically in the FIGURE of the Drawing.

The calcium dependent release of acetylcholine was calculated by subtracting release in the absence of calcium from release in the presence of calcium. Each value represents the mean±S.E.M. of 4 mice per age in triplicate.

Significance was determined by analysis of variance with the least significant difference test (P<0.05).

Example 2 shows that the in vitro calcium dependent release of acetylcholine declined with senescence and the resulting deficit could be ameliorated by administration of 3,4-diaminopyridine. Under depolarizing potassium concentrations, the calcium dependent release decreased 40% between 3 and 10 months and 37% between 10 and 30 months. Release in the absence of calcium was similar at 3 and 10 months, but increased 15% at 30 months. Thus, the calcium dependent potassium stimulated release of acetylcholine declined by 54% between 3 and 10 months of age and decreased 52% between 10 and 30 months. 3,4-diaminopyridine increased acetylcholine release in calcium containing media. In buffer with depolarizing potassium and calcium, 3,4-diaminopyridine improved release by 11, 50 and 92% when compared to non-drug treated 3, 10 and 30 month old mice, respectively. Compared to the 3 month old mice, 3,4-diaminopyridine increased the calcium dependent release of acetylcholine 115% (3 months), 87% (10 months) and 78% (30 months).

Comparison of the results of Example 1 with those of Example 2 shows that the age-related decrease in the release of acetylcholine parallels the decline in the ability to perform a simple behavioral task. Tight rope test behavior declined 46 and 63% in 10 and 30 month old mice compared to 3 month old mice, respectively. This reduction could be diminished by prior treatment with 3,4-diaminopyridine. At 5 minutes after the drug administration, the deficit in behavior was depressed only 16 and 20% in 10 and 30 month old mice, respectively. These percentage decline values were calculated after adding five points (the maximum negative score possible) to all values.

The significant improvement with 3,4-diaminopyridine in behavioral performance and the release of acetylcholine by brain slices from aged mice suggests that interrupted calcium homeostasis may be important in the production of the cholinergic deficits that accompany senescence. We found 3,4-diaminopyridine to be 1,000 times more potent than 4-aminopyridine in reversing the effect of hypoxia. The precise mechanism of action of the aminopyridines is unclear; they may either enhance calcium influx into the nerve terminals directly or indirectly through blockage of potassium channels. These drugs are ineffective in the absence of calcium or in the presence of calcium channel blockers (e.g., tetraethylammonium). Aging and low oxygen may alter the uptake of calcium in the central nervous system, since increased calcium influx by the aminopyridines reduces the inhibition in acetylcholine release and behavior. In stimulated smooth muscle, the hypoxic block of calcium uptake may be due to an alteration in the cellular redox state, which is known to inhibit mitochondrial calcium transport. The changes in calcium homeostasis with aging that alter acetylcholine metabolism remain to be determined.

Variations of the invention will be apparent to the skilled artisan.

What is claimed is:

1. A method to ameliorate decreased cognition occurring with aging in mammals which comprises administering to a mammal suffering from age-related cognition deficiency a cognition-improving amount of an unsubstituted diaminopyridine of the formula

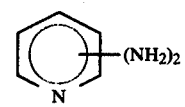

(I)

2. A method to increase release of acetylcholine in the vicinity of nerve tissues which comprises administering to a mammal an unsubstituted diaminopyridine of the formula

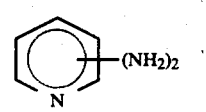

(I)

in an amount sufficient to increase the calcium-dependent, calcium-stimulated release of acetylcholine in the vicinity of nerve tissue.

3. The method of claim 1 or claim 2 wherein the two amino groups are attached to adjacent carbon atoms of the pyridine ring.

4. The process of claim 1 or claim 2 wherein the diaminopyridine is 3,4-diaminopyridine.

5. The process of claims 1 or 2 wherein the diaminopyridine is selected from the group consisting of 2,3-diaminopyridine; 2,5-diaminopyridine; 2,6-diaminopyridine; 3,4-diaminopyridine; 4,5-diaminopyridine and 4,6-diaminopyridine.

6. A pharmaceutical preparation comprising an amount of an unsubstituted diaminopyridine of the formula

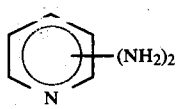
(I)

sufficient to improve age-related cognition deficiency and a pharmaceutically-acceptable carrier.

7. A pharmaceutical preparation comprising an unsubstituted diaminopyridine of the formula

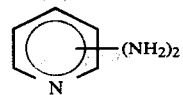
(I)

in an amount sufficient to increase the calcium-dependent potassium-stimulated release of acetylcholine and a pharmaceutically-acceptable carrier.

8. The pharmaceutical preparation of claim 6 or claim 7 wherein the two amino groups are attached to adjacent carbon atoms of the pyridine ring.

9. The pharmaceutical preparation of claim 6 or claim 7 wherein the diaminopyridine is 3,4-diaminopyridine.

10. The pharmaceutical preparation of claims 6 and 7 wherein the diaminopyridine is selected from the group consisting of 2,3-diaminopyridine, 2,5-diaminopyridine; 2,6-diaminopyridine; 3,4-diaminopyridine; 4,5-diaminopyridine and 4,6-diaminopyridine.

* * * * *